United States Patent [19]

Schadt et al.

[11] 4,452,718

[45] Jun. 5, 1984

[54] PYRIDAZINES

[75] Inventors: Martin Schadt, Seltisberg; Kuno Schleich, Zollikerberg, both of Switzerland; Georg Trickes, Grenzach-Wyhlen, Fed. Rep. of Germany

[73] Assignee: Hoffmann-La Roche Inc., Nutley, N.J.

[21] Appl. No.: 396,997

[22] Filed: Jul. 12, 1982

[30] Foreign Application Priority Data

Jul. 31, 1981 [CH] Switzerland .................. 4971/81
May 14, 1982 [CH] Switzerland .................. 3014/82

[51] Int. Cl.³ .................. C09K 3/34; G02F 1/13; C07D 237/02; C07D 237/08
[52] U.S. Cl. .................. 252/299.61; 252/299.5; 252/299.67; 350/346; 350/350 R; 544/224; 544/239
[58] Field of Search .................. 544/224, 239; 252/299.61, 299.5, 299.67; 350/346, 350 R

[56] References Cited

U.S. PATENT DOCUMENTS

| 3,997,536 | 12/1976 | Boller et al. | 252/299.61 |
|---|---|---|---|
| 4,062,798 | 12/1977 | Boller et al. | 252/299.61 |
| 4,273,929 | 6/1981 | Boller et al. | 252/299.61 |
| 4,309,539 | 1/1982 | Boller et al. | 252/299.61 |
| 4,335,011 | 6/1982 | Sethofer | 252/299.61 |
| 4,344,856 | 8/1982 | Demus et al. | 252/299.61 |
| 4,348,298 | 9/1982 | Zaschke et al. | 252/299.61 |
| 4,358,589 | 11/1982 | Schubert et al. | 252/299.61 |
| 4,364,838 | 12/1982 | Boller et al. | 252/299.61 |
| 4,419,262 | 12/1983 | Petrzilka | 252/299.61 |

FOREIGN PATENT DOCUMENTS

| 36711 | 9/1981 | European Pat. Off. | 252/299.61 |
|---|---|---|---|
| 56501 | 7/1982 | European Pat. Off. | 252/299.61 |
| 2257588 | 6/1973 | Fed. Rep. of Germany | 252/299.61 |
| 2085877 | 5/1982 | United Kingdom | 252/299.61 |

OTHER PUBLICATIONS

Nash, J. A. et al., Mol. Cryst. Liq. Cryst., vol. 25, pp. 299–321 (1974).
Schubert, H. et al., Z. Chem., vol. 6, No. 12, p. 467 (1966).
Weygand, C. et al., J. Prakt. Chem., vol. 155, pp. 221–226 (1938).
Zaschke, H. et al., Z. Chem., vol. 17(9), pp. 333–334 (1977).
Schubert, H., Wiss. Z. Univ. Halle XIX'70 M, H. 5, 5.1–18.
Boller, A. et al., Mol. Cryst. Liq. Cryst., vol. 42, No. 1–3, pp. 215–231 (1977).
Gray, G. W., Mol. Cryst. Liq. Cryst., vol. 53, pp. 147–166, (1979).
Gray, G. W., Mol. Cryst. Liq. Cryst., vol. 63, pp. 3–18, (1981).
Chem. Abst. 66:54977e (1967).
Chem. Abst. 10:153,4 (1939).
Chem. Abst. 88:6824k (1978).

Primary Examiner—Teddy S. Gron
Attorney, Agent, or Firm—Jon S. Saxe; Bernard S. Leon; George W. Johnston

[57] ABSTRACT

Compounds of the formula

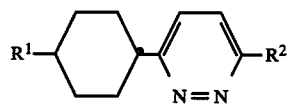

I wherein R¹ is straight-chain alkyl of 1 to 12 carbon atoms, R² is alkyl, alkoxy, p-alkylphenyl, p-alkoxyphenyl or trans-4-alkylcyclohexyl, and the alkyl and alkoxy groups in R² each are straight-chain groups of 1 to 10 carbon atoms, their manufacture, liquid crystalline mixtures containing said compounds as well as their use for electro-optical purposes are described. The novel compounds are valuable components for liquid crystalline mixtures and have a negative dielectric anisotropy.

18 Claims, No Drawings

PYRIDAZINES

BACKGROUND OF THE INVENTION

1. Field of the Invention

This invention relates to liquid crystalline compounds and mixtures.

2. Description of the Prior Art

In an electric field, the molecules of liquid crystalline nematic and cholesteric compounds or mixtures which possess a negative anisotropy of the dielectric constants (i.e. $\epsilon_\| < \epsilon_\perp$) are oriented with their longitudinal axes perpendicular to the field direction. $\epsilon_\|$ signifies the dielectric constant along the longitudinal axis of the molecule and $\epsilon_\perp$ signifies the dielectric constant perpendicular thereto.

This dielectric field effect is used for the control of the optical transmissivity in various liquid crystal indicators. For example, the effect is utilized in liquid crystal cells of the light scattering type (dynamic scattering), of the so-called DAP type or of the guest-host type [guest-host interaction; Applied Physics Letters 13(1968) 91].

These "guest-host cells" comprise essentially a condenser-like structure with at least one electrode plate being transparent and a dielectric being formed from nematic or cholesteric liquid crystal materials which contain one or more dichroic dyes. In the cells, the longitudinal axes of these colouring substances and the liquid crystals align parallel to each other. Since the colouring substances usually have positive dichroism, their transition moment of the absorption of visible light lies approximately in the direction of the longitudinal molecular axis of the dye. That is, one sees a colour when viewing in a direction perpendicular to the longitudinal axis of the dyes. Consequently, the orientation of the liquid crystal and dyes with their molecular axes parallel to the surface of the plates generally corresponds to the coloured state. Also, the homeotropic orientation (longitudinal molecular axes perpendicular to the surface of the plates) generally corresponds to the colourless condition of the cell.

When a liquid crystal with positive dielectric anisotropy is used ($\epsilon_\| > \epsilon_\perp$), its homogeneous orientation (i.e. longitudinal axis of molecules is parallel to surface of electrode, which is achieved by suitably treating the surface of the electrode plates) becomes homeotropic (i.e. longitudinal axis of molecules is perpendicular to surface of the electrodes) by the application of a voltage. Consequently, from the field-off to the field-on state, the cell is switched from "coloured" to "colourless". In this manner, colourless symbols are shown on a coloured background. With a liquid crystal having negative dielectric anisotropy ($\epsilon_\| < \epsilon_\perp$), its homeotropic orientation (i.e. by suitably treating the surface of the electrode plates) is arranged parallel to the electrode surfaces by the application of a voltage. Thus, with the field-on state there results a coloured image elements on a colourless background.

Further, for the improvement of the multiplex ratio in the multiplex control of liquid crystal indicators (especially of rotation cells and guest-host cells), there has been proposed a two-frequency matrix addressing procedure (e.g. German Offenlegungsschriften No. 28 56 134 (Great Britain Pat. No. 2,013,014) and No. 29 07 940 (Great Britain Pat. No. 2,020,075)). This procedure makes use of the fact that the dielectric anisotropy of nematic liquid crystals having a positive anisotropy of the dielectric constants upon application of a low-frequency voltage, is negative in the case of high frequencies. To maintain a relatively low energy consumption, the "cross-over frequency" $f_c$ (dielectric relaxation frequency at which $\epsilon_\| = \epsilon_\perp$) of such liquid crystals should be at most 20 kHz or smaller. Further, the absolute dielectric anisotropies should be as large as possible not only below but also above the cross-over frequency. Disadvantageously, at frequencies above the cross-over frequency, the substances which are especially suitable for the two-frequency procedure generally have a smaller absolute dielectric anisotropy than below the cross-over frequency. This disadvantage, however, can be eliminated by adding one or more compounds with negative dielectric anisotropy and establishing suitable relaxation behavior.

Furthermore, liquid crystals which in the case of high frequencies have a negative dielectric anisotropy can, however, also be controlled by switching-on and switching-off an alternating current of high frequency. The liquid crystals thereby behave as customary liquid crystals with negative anisotropy of the dielectric constants.

A series of liquid crystalline compounds with weakly negative dielectric anisotropy has already hitherto been synthesized. However, still relatively few liquid crystals with large negative anisotropy of the dielectric constants are known. Moreover, the latter generally have disadvantages such as poor stability in mixtures, high melting points, high viscosity, strong smectic tendencies and chemical instability. There accordingly exists a great need for further improved compounds with negative anisotropy of the dielectric constants which can be utilized in a wide variety of display applications.

SUMMARY OF THE INVENTION

The invention relates to pyridazines of the formula

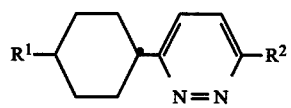

I wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and the alkyl and alkoxy groups in $R^2$ each are straight-chain groups of 1 to 10 carbon atoms.

It has now been found that the compounds of formula I have a large negative anisotropy of the dielectric constants, a good solubility in known liquid crystal mixtures and (especially in the case of the compounds of formula I in which $R^2$ is alkyl or alkoxy) a relatively low viscosity. Further, they are colourless and have a good chemical stability and only slight smectic tendencies. The compounds provided by the invention are therefore especially suitable for improving the properties of liquid crystal mixtures with negative anisotropy of the dielectric constants or of liquid crystal mixtures which are suitable for two-frequency matrix addressing.

The invention is also concerned with the manufacture of the compounds of formula I above, liquid crystalline mixtures containing such compounds as well as their use in electro-optical devices.

DETAILED DESCRIPTION OF THE INVENTION

The present invention is concerned with novel 6-(trans-4-alkylcyclohexyl)pyridazines of the formula

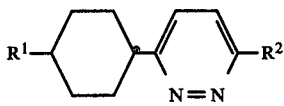

I wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and the alkyl and alkoxy groups in $R^2$ each are straight-chain groups of 1 to 10 carbon atoms.

The compounds provided by the invention are valuable as components of liquid crystalline (especially nematic and cholesteric) mixtures and have a negative anisotropy of the dielectric constants. The inventive compounds are soluble in known liquid crystal mixtures and have a relatively low viscosity. Further, they are colourless and have a good chemical stability and only slight smectic tendencies. The compounds provided by the invention are therefore especially suitable for improving the properties of liquid crystal mixtures with negative anisotropy of the dielectric constants or of liquid crystal mixtures which are suitable for two-frequency matrix addressing. However, they can of course also be used in mixtures with positive dielectric anisotropy in order to adapt the threshold potential to the electro-optical cell which is used.

The compound of formula I in which $R^2$ represents alkyl or alkoxy generally have only monotropic or virtual clearing points. It has, however, surprisingly been found that in mixtures they give only slight clearing point depressions, whereas the melting points can be considerably lowered eutectic.

The remaining compounds of formula I (i.e. those in which $R^2$ represents p-alkylphenyl, p-alkoxyphenyl or trans-4-alkylcyclohexyl) have, on the other hand, for the most part enantiotropic clearing points and in many cases a large mesophase range with high clearing points. Although these compounds generally form in the pure form smectic mesophases, they are surprisingly very well suited as mixture components for nematic and cholesteric mixtures.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl octyl, nonyl, decyl, undecyl and dodecyl. Exemplary branched-chain alkyl groups are isopropyl, isobutyl, sec-butyl, 1-methylbutyl, 2-methylbutyl 3-methylpentyl, 4-methylhexyl and isopentyl. Lower alkyl denotes straight-chain and branched-chain alkyl groups of 1 to 5 carbon atoms. The alkyl group $R^1$ can contain 1 to 12 carbon atoms.

The terms "alkoxy", "alkanoyloxy", "p-alkylphenyl", "p-alkoxyphenyl" and "trans-4-alkylcyclohexyl" as well as the other groups in the specification containing "alkyl" denote moieties in which their "alkyl" portions are as defined previously. In particular, straight-chain alkoxy groups denote moieties having a straight-chain alkyl portion as previously defined. Moreover, the group $R^2$ of formula I embraces those alkyl, alkoxy, p-alkylphenyl, p-alkoxyphenyl and trans-4-alkylcyclohexyl groups in which alkyl and alkoxy are straight-chain alkyl or alkyloxy groups of 1 to 10 carbon atoms and alkyl has the significance given earlier.

The term "halogen" denotes fluorine, chlorine, bromine or iodine.

The term "alkali metal" denotes sodium, potassium or lithium.

Preferred compounds of formula I are those in which $R^2$ represents alkyl, alkoxy or p-alkylphenyl. Furthermore, there are preferred those compounds of formula I in which the alkyl or alkoxy group present in $R^2$ is a straight-chain group containing 1 to 7 carbon atoms. Preferred $R^1$ groups are straight-chain alkyl groups containing 3 to 9 carbon atoms and especially those containing 3 to 7 carbon atoms. Accordingly, especially preferred compounds of formula I are those in which $R^1$ represents a straight-chain alkyl group containing 3 to 7 carbon atoms and $R^2$ represents a straight-chain alkyl or alkoxy group containing 1 to 7 carbon atoms or a phenyl group which is substituted in the p-position by a straight-chain alkyl group containing 1 to 7 carbon atoms.

The following are examples of preferred compounds of formula I:

3-Methyl-6-(trans-4-pentylcyclohexyl)pyridazine,
3-methyl-6-(trans-4-heptylcyclohexyl)pyridazine,
3-ethyl-6-(trans-4-pentylcyclohexyl)pyridazine,
3-ethyl-6-(trans-4-heptylcyclohexyl)pyridazine,
3-propyl-6-(trans-4-propylcyclohexyl)pyridazine,
3-propyl-6-(trans-4-butylcyclohexyl)pyridazine,
3-propyl-6-(trans-4-pentylcyclohexyl)pyridazine,
3-propyl-6-(trans-4-hexylcyclohexyl)pyridazine,
3-propyl-6-(trans-4-heptylcyclohexyl)pyridazine,
3-butyl-6-(trans-4-propylcyclohexyl)pyridazine,
3-butyl-6-(trans-4-pentylcyclohexyl)pyridazine,
3-butyl-6-(trans-4-heptylcyclohexyl)pyridazine,
3-pentyl-6-(trans-4-propylcyclohexyl)pyridazine,
3-pentyl-6-(trans-4-butylcyclohexyl)pyridazine,
3-pentyl-6-(trans-4-pentylcyclohexyl)pyridazine,
3-pentyl-6-(trans-4-hexylcyclohexyl)pyridazine,
3-pentyl-6-(trans-4-heptylcyclohexyl)pyridazine,
3-hexyl-6-(trans-4-propylcyclohexyl)pyridazine,
3-hexyl-6-(trans-4-pentylcyclohexyl)pyridazine,
3-heptyl-6-(trans-4-propylcyclohexyl)pyridazine,
3-heptyl-6-(trans-4-pentylcyclohexyl)pyridazine,
3-octyl-6-(trans-4-pentylcyclohexyl)pyridazine,
3-methoxy-6-(trans-4-pentylcyclohexyl)pyridazine,
3-methoxy-6-(trans-4-heptylcyclohexyl)pyridazine,
3-ethoxy-6-(trans-4-propylcyclohexyl)pyridazine,
3-ethoxy-6-(trans-4-butylcyclohexyl)pyridazine,
3-ethoxy-6-(trans-4-pentylcyclohexyl)pyridazine,
3-ethoxy-6-(trans-4-hexylcyclohexyl)pyridazine,
3-ethoxy-6-(trans-4-heptylcyclohexyl)pyridazine,
3-propyloxy-6-(trans-4-propylcyclohexyl)pyridazine,
3-propyloxy-6-(trans-4-pentylcyclohexyl)pyridazine,
3-butyloxy-6-(trans-4-propylcyclohexyl)pyridazine,
3-butyloxy-6-(trans-4-butylcyclohexyl)pyridazine,
3-butyloxy-6-(trans-4-pentylcyclohexyl)pyridazine,
3-pentyloxy-6-(trans-4-propylcyclohexyl)pyridazine,
3-pentyloxy-6-(trans-4-butylcyclohexyl)pyridazine,
3-pentyloxy-6-(trans-4-pentylcyclohexyl)pyridazine,
3-hexyloxy-6-(trans-4-propylcyclohexyl)pyridazine,
3-hexyloxy-6-(trans-4-pentylcyclohexyl)pyridazine,
3-(p-methylphenyl)-6-(trans-4-pentylcyclohexyl)pyridazine,
3-(p-ethylphenyl)-6-(trans-4-pentylcyclohexyl)pyridazine, 3-(p-propylphenyl)-6-(trans-4-propylcyclohexyl)-pyridazine,
3-(p-propylphenyl)-6-(trans-4-pentylcyclohexyl)pyridazine,
3-(p-propylphenyl)-6-(trans-4-heptylcyclohexyl)pyridazine,
3-(p-butylphenyl)-6-(trans-4-pentylcyclohexyl)pyridazine,
3-(p-pentylphenyl)-6-(trans-4-propylcyclohexyl)pyridazine,
3-(p-pentylphenyl)-6-(trans-4-butylcyclohexyl)pyridazine,
3-(p-pentylphenyl)-6-(trans-4-pentylcyclohexyl)pyridazine,
3-(p-pentylphenyl)-6-(trans-4-hexylcyclohexyl)pyridazine,
3-(p-pentylphenyl)-6-(trans-4-heptylcyclohexyl)pyridazine,
3-(p-hexylphenyl)-6-(trans-4-propylcyclohexyl)pyridazine,
3-(p-hexylphenyl)-6-(trans-4-pentylcyclohexyl)pyridazine,
3-(p-heptylphenyl)-6-(trans-4-propylcyclohexyl)pyridazine,
3-(p-heptylphenyl)-6-(trans-4-pentylcyclohexyl)pyridazine,
3-(p-ethoxyphenyl)-6-(trans-4-pentylcyclohexyl)-pyridazine,
3-(p-ethoxyphenyl)-6-(trans-4-heptylcyclohexyl)-pyridazine,
3-(p-propyloxyphenyl)-6-(trans-4-propylcyclohexyl)-pyridazine,
3-(p-propyloxyphenyl)-6-(trans-4-pentylcyclohexyl)-pyridazine,
3-(p-butyloxyphenyl)-6-(trans-4-propylcyclohexyl)-pyridazine,
3-(p-butyloxyphenyl)-6-(trans-4-pentylcyclohexyl)-pyridazine,
3-(p-butoxyphenyl)-6-(trans-4-heptylcyclohexyl)-pyridazine,
3-(p-pentyloxyphenyl)-6-(trans-4-pentylcyclohexyl)-pyridazine,
3-(p-hexyloxyphenyl)-6-(trans-4-propylcyclohexyl)-pyridazine,
3-(p-hexyloxyphenyl)-6-(trans-4-pentylcyclohexyl)-pyridazine,
3-(trans-4-ethylcyclohexyl)-6-(trans-4-pentylcyclohexyl)pyridazine,
3-(trans-4-propylcyclohexyl)-6-(trans-4-pentylcyclohexyl)pyridazine,
3-(trans-4-propylcyclohexyl)-6-(trans-4-heptylcyclohexyl)pyridazine,
3-(trans-4-butylcyclohexyl)-6-(trans-4-pentylcyclohexyl)pyridazine,
3-(trans-4-pentylcyclohexyl)-6-(trans-4-propylcyclohexyl)pyridazine,
3-(trans-4-pentylcyclohexyl)-6-(trans-4-butylcyclohexyl)pyridazine,
3,6-bis(trans-4-pentylcyclohexyl)pyridazine,
3-(trans-4-pentylcyclohexyl)-6-(trans-4-hexylcyclohexyl)pyridazine,
3-(trans-4-pentylcyclohexyl)-6-(trans-4-heptylcyclohexyl)pyridazine,
3-(trans-4-hexylcyclohexyl)-6-(trans-4-pentylcyclohexyl)pyridazine,
3-(trans-4-heptylcyclohexyl)-6-(trans-4-propylcyclohexyl)pyridazine,
3-(trans-4-heptylcyclohexyl)-6-(trans-4-pentylcyclohexyl)pyridazine,
3-propyl-6-(trans-4-ethylcyclohexyl)pyridazine.

The compounds of formula I can be manufactured in accordance with the invention by (a) for the manufacture of the compounds of formula I in which $R^2$ represents an alkyl, p-alkylphenyl, p-alkoxyphenyl or trans-4-alkylcyclohexyl group, oxidizing a compound of the formula

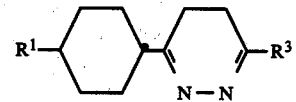

II wherein $R^3$ is alkyl, p-alkylphenyl, p-alkoxyphenyl or trans-4-alkylcyclohexyl, the alkyl and alkoxy groups in $R^3$ are straight-chain groups of 1 to 10 carbon atoms and $R^1$ has the significance given earlier, or a tautomeric dihydropyridazine, or (b) for the manufacture of the compounds of formula I in which $R^2$ represents an alkoxy group, reacting a compound of the formula

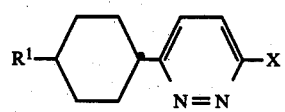

III wherein X is chlorine or bromine and $R^1$ has the significance given earlier, with an alkali metal alcoholate, The oxidation of a compound of formula II in accordance with process variant (a) can be carried out in a manner known per se; for example, with 2,3-dichloro-5,6-dicyano-p-benzoquinone in dioxan, with sodium nitrite in glacial acetic acid and ethanol, with isopentyl nitrite in glacial acetic acid and the like. Temperature and pressure are not critical aspects in this reaction. However, atmospheric pressure and a temperature between about room temperature (23° C.) and the reflux temperature, preferably about room temperature, are conveniently used. The compounds of formula II are, however, preferably oxidized to compounds of formula I by catalytic dehydrogenation in a manner known per se. The dehydrogenation can be carried out with any catalyst which are usually used in dehydrogenation reactions, examples of such catalysts being palladium, platinum and the like (optionally on an inert carrier material such as carbon). Palladium is the preferred catalyst. As the solvent there can be used any inert organic solvent such as alcohols, ethers, esters, carboxylic acids and the like, for example ethanol, dioxan, ethyl acetate or glacial acetic acid. Ethanol is the preferred solvent. Temperature and pressure are not critical aspects in this reaction. A temperature between about room temperature (23° C.) and the reflux temperature of the reaction mixture and atmospheric pressure are conveniently used.

The compounds of formula II can rearrange to tautomeric compounds by migration of the double bonds in the dihydropyridazine ring. Such rearrangements can be brought about, for example, by the presence of a trace of acid or base (e.g. hydrochloric acid, sodium hydroxide). Since, however, the tautomeric dihydropyridazines can also be oxidized to compounds of formula I under the aforementioned conditions, not only a compound of formula II, but also a tautomeric dihydropyridazine or a mixture of such compounds can be used in process variant (a).

The reaction of a compound of formula III with an alkali metal alcoholate in accordance with process variant (b) can be carried out in a manner known per se. Sodium is the preferred alkali metal. As the solvent there can be used any inert organic solvent such as ethers, saturated or aromatic hydrocarbons and the like, for example benzene, toluene, hexane, diethyl ether or dioxan. Preferably, however, the alcohol corresponding to the alcoholate is used as the solvent (optionally in combination with an inert organic solvent). In this case, the alcoholic solution of the alcoholate is conveniently prepared by reacting an excess of the alcohol with sodium, sodium hydride, potassium hydride and the like. Temperature and pressure are not critical aspects in the reaction of the compounds of formula III with an alkali metal alcoholate. Atmospheric pressure and a temperature between about room temperature (23° C.) and the reflux temperature of the reaction mixture, preferably about 40° to about 60° C., are conveniently used.

The starting materials of formulae II and III are novel and also form objects of the present invention. They can be prepared according to Reaction Schemes A–D hereinafter in which $R^1$, $R^3$ and X have the significances given earlier and $R^4$ is a straight-chain alkyl or alkoxy of 1 to 10 carbon atoms.

Scheme A

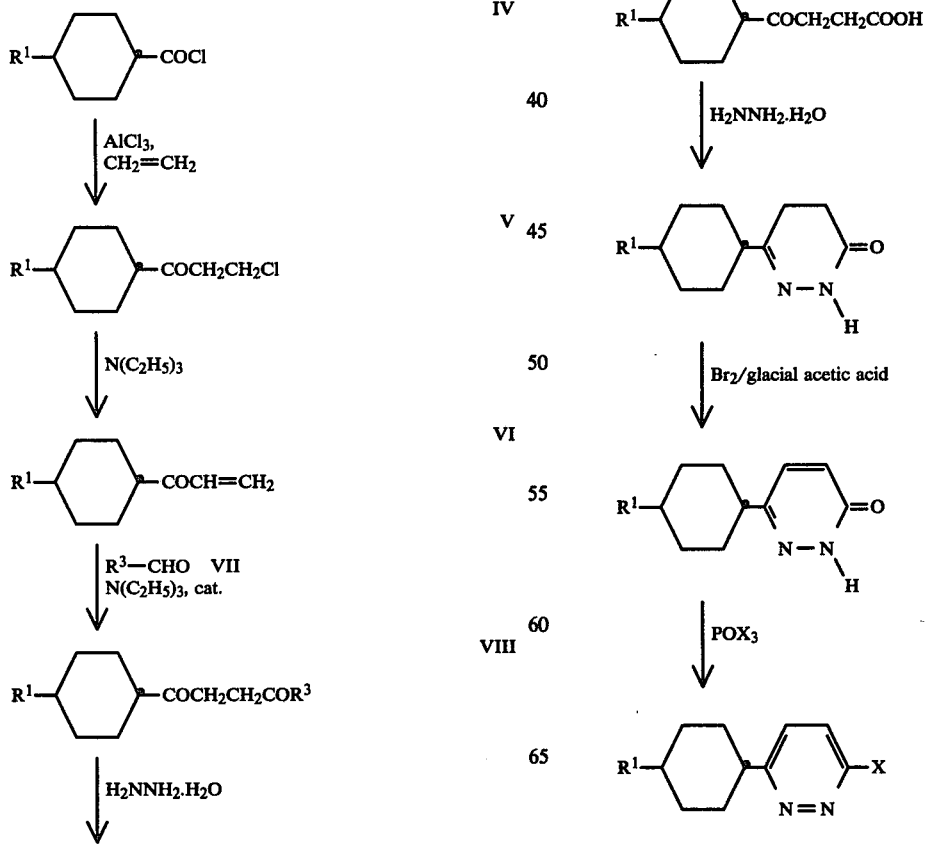

-continued
Scheme A

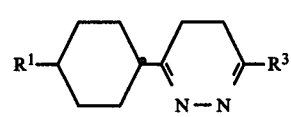

II

Scheme B

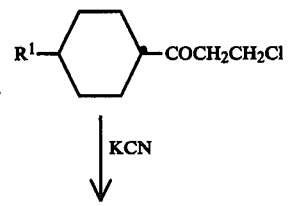

↓ KCN

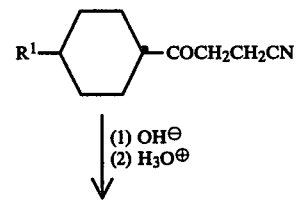

↓ (1) OH⊖
 (2) $H_3O^⊕$

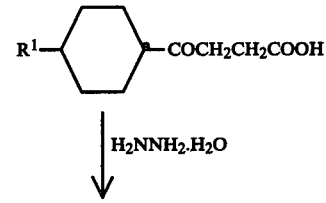

↓ $H_2NNH_2 \cdot H_2O$

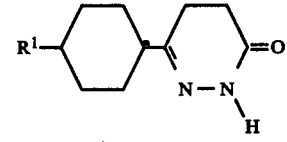

↓ $Br_2$/glacial acetic acid

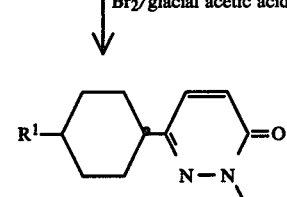

↓ $POX_3$

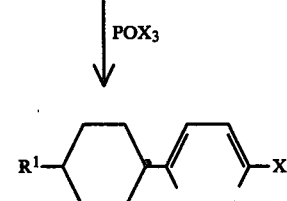

Scheme C

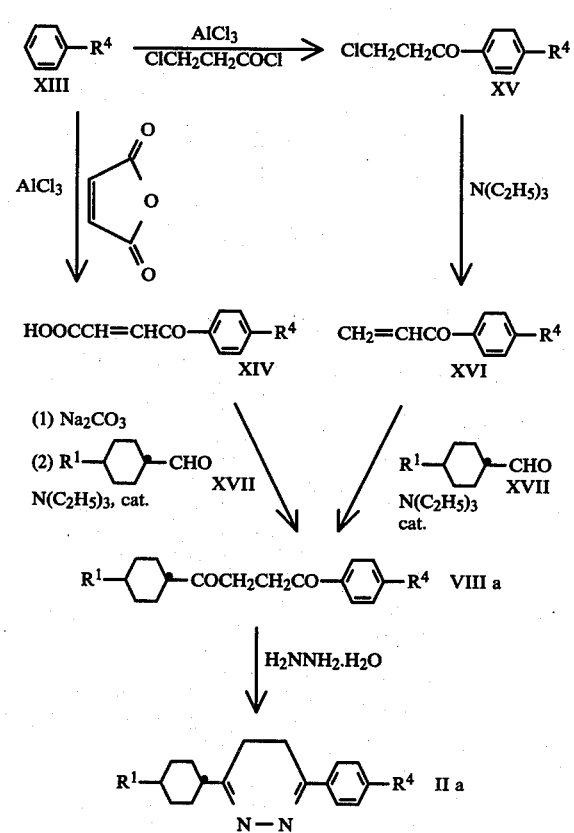

Scheme D

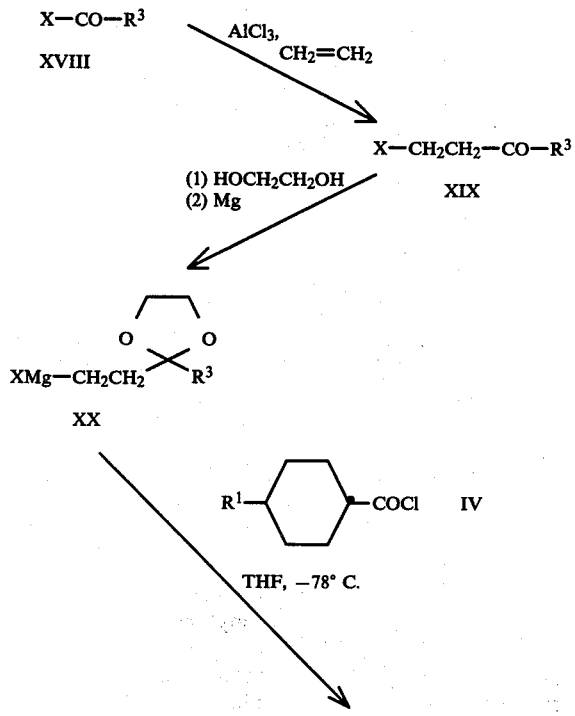

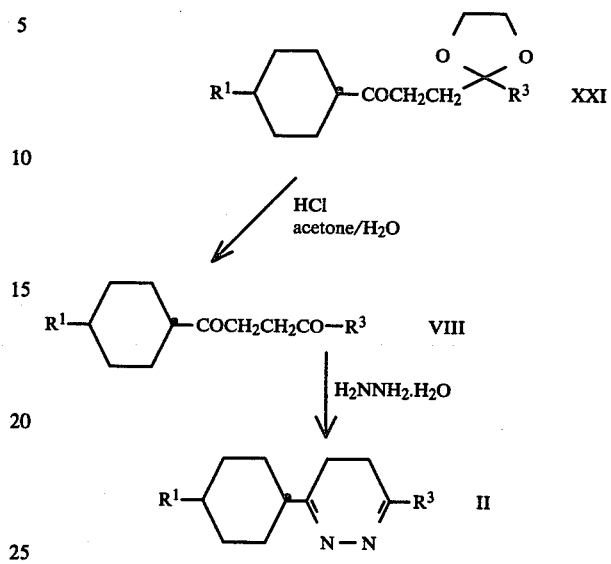

-continued
Scheme D

The compounds of formulae IV, VII, XIII, XVII and XVIII are known compounds or are analogues of known compounds and can be prepared from known compounds in a known manner. For example, the aldehydes of formula XVII can be prepared by a Rosenmund reduction of the acid chlorides of formula IV.

The addition of an aldehyde to a compound of formula VI, XIV or XVI can be carried out according to the method of Stetter [Chem. Ber. 114 (1981) 581] in the presence of a 1,3-thiazolium salt catalyst. 3-Benzyl-5-(2-hydroxyethyl)-4-methyl-1,3-thiazolium chloride is the preferred catalyst for the addition of an aldehyde of formula XVII or of an aldehyde of formula VII in which $R^3$ represents alkyl or trans-4-alkylcyclohexyl. 3,4-dimethyl-5-(2-hydroxyethyl)-1,3-thiazolium iodide is the preferred catalyst for the addition of an aldehyde of formula VII in which $R^3$ represents p-alkylphenyl or p-alkoxyphenyl.

The coupling of a compound of formula XX with a compound of formula IV can be carried out according to the method described by T. Sato et al in Bull. Chem. Soc. Japan 54 (1981) 505.

The compounds of formula II can also be prepared according to a process which differs from the process described in Scheme A only by interchanging the trans-4-$R^1$-cyclohexyl group and the group $R^3$.

As mentioned earlier, the compounds of formula II can also be present in tautomeric form or as a mixture of tautomeric forms.

The compounds provided by the invention can be used in the form of mixtures with other liquid crystalline or non-liquid crystalline substances such as, for example, with substances from the classes of Schiffs' bases, azobenzenes, azoxybenzenes, phenyl benzoates, cyclohexanecarboxylic acid phenyl esters and cyclohexyl esters, biphenyls, terphenyls, phenylcyclohexanes, cinnamic acid derivatives, phenylpyrimidines, diphenylpyrimidines, phenyldioxanes, cyclohexylphenylpyrimidines, phenylbicyclo[2.2.2]octanes, 1-phenyl-2-cyclohexylethanes, derivatives of hydroquinone and 4-hydroxybenzoic acid and the like. Such compounds are known to a person skilled in the art and many of them are, moreover, commercially available.

In principle, the compounds provided by the invention can be used in mixtures for any liquid crystal indicators, thus, for example, even in liquid crystal mixtures with positive dielectric anisotropy for the purpose of adjusting the dielectric anisotropies of the mixtures utilized in the cell. The compounds provided by the invention are, however, preferably used in mixtures with negative dielectric anisotropy or in mixtures with frequency-dependent dielectric anisotropy which are suitable for the two-frequency control procedure.

The liquid crystal mixtures provided by the invention for the two-frequency control contain, in addition to one or more compounds of formula I, preferably a nematic matrix with a dielectric anisotropy of about −3 to about +1 and one or more components with low crossover frequency (about 100 Hz to about 20 kHz) and strongly positive dielectric anisotropy ($\Delta\epsilon > 10$) at frequencies which lie clearly below the cross-over frequency of the total mixture. Preferred examples of the last-mentioned compounds are the phenyl benzoates and diesters of 2-chloro-4-hydroxybenzoic acid disclosed in German Offenlegungsschrift No. 30 26 965 (Great Britain Pat. No. 2,058,050) and especially the p-(2,2-dicyanovinyl)phenyl esters of the formula

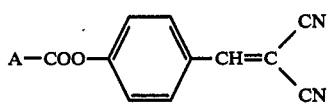

XXII wherein A represents a group of the formula

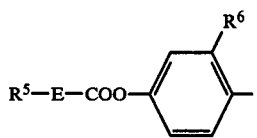

XXIII or a group of the formula

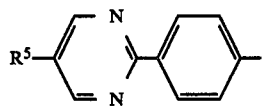

XXIV wherein $R^5$ alone is straight-chain alkyl of 1 to 12 carbon atoms and $R^6$ is fluorine, chlorine, bromine or cyano and $R^5$—E is p-alkylphenyl, trans-4-alkylcyclohexyl, 4′-alkyl-4-biphenylyl, p-(trans-4-alkylcyclohexyl)phenyl or p-(5-alkyl-2-pyrimidinyl)phenyl.

The aforementioned nematic matrix with a dielectric anisotropy of about −3 to about +1 preferably contains one or more of the following compounds:

Trans-4-alkylcyclohexanecarboxylic acid p-alkoxyphenyl esters of the formula

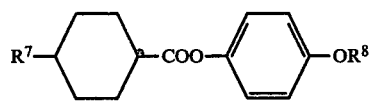

XXV wherein $R^7$ and $R^8$ each are straight-chain alkyl of 1 to 8 carbon atoms, trans-4-alkyl-1-(p-alkylphenyl)cyclohexanes of the formula

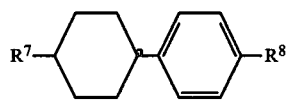

XXVI wherein $R^7$ and $R^8$ are as above,
4,4′-dialkylbiphenyls of the formula

XXVII wherein $R^7$ and $R^8$ are as above,
trans-4-alkylcyclohexanecarboxylic acid trans-4-alkylcyclohexyl esters fo the formula

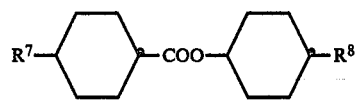

XXVIII wherein $R^7$ and $R^8$ are as above,
p-alkylbenzylidene-p′-alkylanilines of the formula

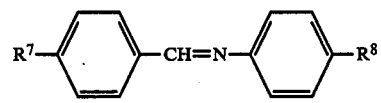

XXIX wherein $R^7$ and $R^8$ are as above,
4-alkyl-1-(p-alkylphenyl)bicyclo[2.2.2]octanes of the formula

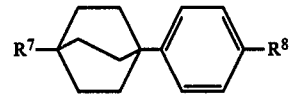

XXX wherein $R^7$ and $R^8$ are as above,
(trans-4-alkylcyclohexyl)ethanes of the formula

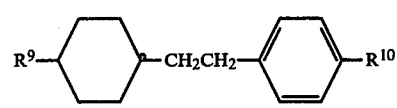

XXXI wherein $R^{10}$ is —$R^{11}$ or —$OR^{11}$ and $R^9$ and $R^{11}$ each are straight-chain alkyl of 1 to 12 carbon atoms,
phenyl benzoates of the formula

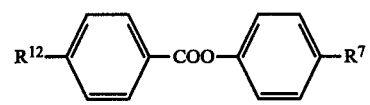

XXXII wherein $R^{12}$ is straight-chain alkyl of 1 to 8 carbon atoms or straight-chain alkanoyloxy of 2 to 9 carbon atoms and $R^7$ is as above,
p-(trans-4-alkylcyclohexyl)benzoic acid trans-4-alkylcyclohexyl esters of the formula $$R^7-\bigcirc-\bigcirc-COO-\bigcirc-R^8 \qquad \text{XXXIII}$$

wherein $R^7$ and $R^8$ are as above,
p-(trans-4-alkylcyclohexylcarbonyloxy)benzoic acid trans-4-alkylcyclohexyl esters of the formula $$R^7-\bigcirc-COO-\bigcirc-COO-\bigcirc-R^8 \qquad \text{XXXIV}$$

wherein $R^7$ and $R^8$ are as above,
and/or trans-4-alkylcyclohexanecarboxylic acid trans-4-(p-alkylphenyl)cyclohexyl esters of the formula $$R^7-\bigcirc-COO-\bigcirc-\bigcirc-R^8 \qquad \text{XXXV}$$

wherein $R^7$ and $R^8$ are as above.

The mixtures provided by the invention for the two-frequency control contain, of the compounds of formula I, preferably those in which $R^2$ represents alkyl or alkoxy.

The compounds of formulae XXII and XXXI hereinbefore are novel.

The compounds of formula XXII can be prepared by esterifying an acid of the formula $$A-COOH \qquad \text{XXXVI}$$

wherein A is a group of formulae XXIII or XXIV as described hereinbefore, $R^6$ is fluorine, chlorine or bromine and $R^5$—E has the significances given earlier,
or a reactive derivative thereof with the compound of the formula $$HO-\bigcirc-CH=C\begin{smallmatrix}CN\\CN\end{smallmatrix} \qquad \text{XXXVII}$$

and, if desired, reacting a resulting compound of formula XXII in which A represents a group of formula XXIII and $R^6$ represents bromine with copper (I) cyanide, sodium cyanide or potassium cyanide.

The esterification of an acid of formula XXXVI or of a reactive derivative thereof (e.g. acid chloride or anhydride) with the phenol of formula XXXVII can be carried out in a manner known per se. Preferred methods are, insofar as A represents a group of formula XXIII, the reaction of the acid chloride (which can be obtained from the acid of formula XXXVI, for example, by heating with thionyl chloride) with the phenol of formula XXXVII and, insofar as A represents a group of formula XXIV, the reaction of the acid of formula XXXVI with the phenol of formula XXXVII in the presence of 4-(dimethylamino)pyridine and N,N'-dicyclohexylcarbodiimide. The reaction of a compound of formula XXII in which A represents a group of formula XXIII and $R^6$ represents bromine to give the corresponding compound in which $R^6$ represents cyano can also be carried out in a manner known per se. The reaction with copper (I) cyanide in dimethylformamide is preferred.

The compounds of formula XXXVI in which A represents a group of formula XXIII and $R^5$—E represents p-alkylphenyl or trans-4-alkylcyclohexyl are known compounds or are analogues of known compounds. The remaining compounds of formula XXXVI, i.e. those in which A represents a group of formula XXIII and $R^5$—E represents 4'-alkyl-4-biphenylyl, p-(trans-4-alkylcyclohexyl)phenyl or p-(5-alkyl-2-pyrimidinyl)phenyl and those in which A represents a group of formula XXIV are on the other hand novel. They possess for the most part liquid crystalline properties also.

The compounds of formula XXXVI in which A represents a group of formula XXIII can be obtained according to Reaction Scheme 1 hereinafter in which $X^1$ represents fluorine, chlorine or bromine and $R^5$—E has the significances given earlier:

Scheme 1

$$R^5-E-COOH + HO-\bigcirc-CHO$$

XXXVIII       XXXIX

↓ 4-(Dimethylamino)pyridine
  N,N'—Dicyclohexylcarbodiimide $$R^5-E-COO-\bigcirc\!\!\!\!\!\!{}^{X^1}\!\!\!-CHO \qquad \text{XL}$$

↓ $H_2SO_4$, $H_2CrO_4$
  Jones' oxidation $$R^5-E-COO-\bigcirc\!\!\!\!\!\!{}^{X^1}\!\!\!-COOH \qquad \text{XXXVIa}$$

The acids of formula XXXVI in which A represents a group of formula XXIV can be prepared in a manner known per se by subjecting the known, liquid crystalline p-(5-alkyl-2-pyrimidinyl)benzonitriles to saponification (e.g. by heating with potassium hydroxide in ethylene glycol and subsequent addition of a mineral acid).

The compounds of formula XXXI can be prepared by reducing a compound of the formula $$R^9-\bigcirc-CH_2-CO-\bigcirc-R^{10} \qquad \text{XLI}$$

wherein $R^9$ and $R^{10}$ have the significances given earlier, in a manner known per se; for example, by Clemmensen reduction or with hydrazine according to the Huang-Minlon process. The compounds of formula XLI can be obtained by Friedel-Crafts acylation of an alkyl- or alkoxybenzene with the acid chloride of a (trans-4-alkylcyclohexyl)acetic acid.

The mixtures provided by the invention with negative dielectric anisotropy conveniently contain in addition to one or more compounds of formula I one or more other compounds with negative and/or small positive anisotropy of the dielectric constants (compounds with positive dielectric anisotropy may be used in the application discussed here in accordance with definition only in amounts which do not leave the anisotropy of the total mixture positive), preferably a nematic compound or mixture having a dielectric anisotropy of at most about +1. Examples of preferred mixture components are the 2,3-dicyano-hydroquinone derivatives described in German Offenlegungsschrift No. 29 37 700 (U.S. Pat. No. 4,279,770) and the compounds of formulae XXV-XXXV hereinbefore.

The amount of the compounds of formula I in the mixtures provided by the invention can amount to about 1 to about 95 mol percent, preferably about 10 to about 60 mol percent. In mixtures which contain compounds of formula I in which $R^2$ represents alkyl or alkoxy, the amount of these compounds should, however, lie between about 1 and about 70 mol percent, preferably between about 10 and about 40 mol percent. If a mixture contains compounds of formula I in which $R^2$ represents p-alkylphenyl, p-alkoxyphenyl or trans-4-alkylcyclohexyl, then the amount of these compounds conveniently amounts to about 1 to about 25 mol percent and preferably about 3 to about 15 mol percent.

The mixtures in accordance with the invention can contain, in addition, optically active compounds (e.g. optically active biphenyls) and/or dichroic colouring substances (e.g. azo, azoxy or anthraquinone colouring substances). The amount of such compounds is determined by the solubility and the desired pitch, colour, extinction and the like. However, the amount of optically active compounds and colouring substances generally lies in each case between about 0.1 and about 10 mol percent. Of course, such additives can, however, also be absent.

The manufacture of the liquid crystalline mixtures provided by the invention can be carried out in a manner known per se; for example, by heating a mixture of the components to a temperature barely above the clearing point and subsequently cooling down.

The manufacture of an electro-optical device containing one or more compounds of formula I can also be carried out in a manner known per se; for example, by evacuating a suitable cell and introducing the corresponding compound or mixture into the evacuated cell.

The invention is also concerned with all novel compounds, mixtures, processes, uses and devices as herein described.

The following Mixture Examples 1-3 illustrate preferred mixtures. C signifies crystalline, S signifies smectic, N signifies nematic, Ch signifies cholesteric and I signifies isotropic phase. The transition points are also denoted correspondingly (e.g. N-I for the clearing points of a nematic liquid crystal).

EXAMPLE 1

17.39 mol % of trans-4-butylcyclohexanecarboxylic acid p-ethoxyphenyl ester,
20.41 mol % of trans-4-butylcyclohexanecarboxylic acid p-pentyloxyphenyl ester,
15.88 mol % of trans-4-pentylcyclohexanecarboxylic acid p-methoxyphenyl ester,
21.17 mol % of trans-4-pentylcyclohexanecarboxylic acid p-propyloxyphenyl ester,
9.45 mol % of 3-propyl-6-(trans-4-pentylcyclohexyl)-pyridazine,
7.46 mol % of 3-propyl-6-(trans-4-heptylcyclohexyl)-pyridazine,
5.50 mol % of 3-heptyl-6-(trans-4-propylcyclohexyl)-pyridazine,
2.74 mol % of 3-ethoxy-6-(trans-4-pentylcyclohexyl)-pyridazine;
C-N about 0° C.; N-I 52° C.; $\Delta\epsilon$ (20° C.)= −4.44.

EXAMPLE 2

16.04 mol % of trans-4-butylcyclohexanecarboxylic acid p-ethoxyphenyl ester,
18.83 mol % of trans-4-butylcyclohexanecarboxylic acid p-pentyloxyphenyl ester,
14.65 mol % of trans-4-pentylcyclohexanecarboxylic acid p-methoxyphenyl ester,
19.54 mol % of trans-4-pentylcyclohexanecarboxylic acid p-propyloxyphenyl ester,
11.63 mol % of 3-propyl-6-(trans-4-pentylcyclohexyl)-pyridazine,
9.18 mol % of 3-propyl-6-(trans-4-heptylcyclohexyl)-pyridazine,
6.76 mol % of 3-heptyl-6-(trans-4-propylcyclohexyl)-pyridazine,
3.37 mol % of 3-ethoxy-6-(trans-4-pentylcyclohexyl)-pyridazine;
C-N about 0° C.; N-I 47° C.; $\Delta\epsilon$ (20° C.)= −5.9.

EXAMPLE 3

16.33 mol % of trans-4-butylcyclohexanecarboxylic acid p-ethoxyphenyl ester,
19.17 mol % of trans-4-butylcyclohexanecarboxylic acid p-pentyloxyphenyl ester,
14.91 mol % of trans-4-pentylcyclohexanecarboxylic acid p-methoxyphenyl ester,
19.88 mol % of trans-4-pentylcyclohexanecarboxylic acid p-propyloxyphenyl ester,
6.97 mol % of 3-propyl-6-(trans-4-pentylcyclohexyl)-pyridazine,
3.48 mol % of 3-propyl-6-(trans-4-heptylcyclohexyl)-pyridazine,
7.89 mol % of 3-pentyl-6-(trans-4-pentylcyclohexyl)-pyridazine,
4.88 mol % of 3-heptyl-6-(trans-4-propylcyclohexyl)-pyridazine,
6.49 mol % of 3-(p-pentylphenyl)-6-(trans-4-propylcyclohexyl)pyridazine;
C-N about 0° C.; cl.p. 64° C.

The following non-limiting Examples 4–6 illustrate the preparation of the compounds of formula I in accordance with the invention. Unless otherwise stated, percentages and ratios are given in volume and the temperatures are expressed in degrees Centigrade. Room temperature is about 23° C. and the ether is diethyl ether. Unless otherwise indicated, the Examples were actually performed as written.

EXAMPLE 4

10.0 g of 2,3-dichloro-5,6-dicyano-p-benzoquinone were dissolved in 100 ml of absolute dioxan in a sulphonation flask with stirrer, thermometer, reflux condenser and nitrogen gasification and a solution of 12.6 g of 4,5-dihydro-3-pentyl-6-(trans-4-pentylcyclohexyl)-pyridazine in 100 ml of absolute dioxan was added slowly (within 20 minutes) through a dropping funnel.

The temperature thereby increased to 35° C. and the mixture became deep brown in colour. After completion of the addition, the mixture was boiled at reflux for 1.5 hours, then cooled to room temperature, the solvent was evaporated completely and the residue was extracted in a Soxhlet with hexane for 1.5 hours. After evaporation of the solvent, the residue was chromatographed on silica gel with chloroform as the eluant, there being obtained 9.3 g of dark brown crystals. These were recrystallized from a mixture of 10 ml of absolute ethanol and 40 ml of low-boiling petroleum ether by cooling to −40° C. and there were obtained 2.1 g of light crystals. The mother liquor was concentrated and the residue was recrystallized from a mixture of 1 ml of absolute ethanol and 9 ml of low-boiling petroleum ether at −20° C., a further 2.4 g of light crystals being obtained. The mother liquor was again concentrated and the residue was recrystallized from 6 ml of low-boiling petroleum ether at −20° C., 2.3 g of light brown crystals being obtained. The three crystallizates obtained and a further 2.1 g of substance from another batch (total 8.9 g) were dissolved in 50 ml of methanol and stirred with active carbon for 30 minutes. After filtration and evaporation, the residue was recrystallized from a mixture of 2 ml of absolute ethanol and 18 ml of low-boiling petroleum ether at −20° C. 4.5 g of white crystals were thereby obtained. A further 2.9 g of white crystals could be isolated from the mother liquor by recrystallization with 6 ml of low-boiling petroleum ether at −20° C. Both crystallizates (7.4 g) were dissolved in 30 ml of methylene chloride, filtered, evaporated and again recrystallized from a mixture of 1.5 ml of isopropanol and 15 ml of pentane at −20° C. There were obtained 6.6 g of white 3-pentyl-6-(trans-4-pentylcyclohexyl)pyridazine which was dried in a high vacuum at room temperature in a weak nitrogen stream. C-I 76.3° C.; virtual cl.p. about 3°–4° C.; Rf value (chloroform/acetone 10:1) 0.57.

The 4,5-dihydro-3-pentyl-6-(trans-4-pentylcyclohexyl)pyridazine used as the starting material was prepared as follows:

(a) 32.0 g of aluminium chloride were suspended in 150 ml of methylene chloride in a sulphonation flask with stirrer, gas inlet tube, low temperature thermometer, reflux condenser, dropping funnel and nitrogen gasification, cooled to 0° C. and then 43.3 g of trans-4-pentylcyclohexanecarboxylic acid chloride were added dropwise at 0° to 10° C. within 10 minutes. The mixture was stirred for a further 30 minutes while introducing nitrogen, then cooled to −10° C. and ethylene was introduced up to saturation. After completion of the reaction (about 3 hours), the excess ethylene was driven off with nitrogen and the batch was hydrolyzed by (dropwise at the beginning) addition of 70 ml of 1 N hydrochloric acid so that the internal temperature did not rise above 20° C. (strong cooling required). After separation of the organic phase, the aqueous solution was extracted with 100 ml of methylene chloride. The combined organic phases were washed with 150 ml of water, dried over sodium sulphate and concentrated at 30° C. on a rotary evaporator. The yellow coloured crude product obtained was recrystallized from 50 ml of ethanol at −20° C. Yield: 31.15 g (64%) of white crystals of 1-(trans-4-pentylcyclohexyl)-3-chloropropan-1-one; m.p. 42°–43° C.; Rf value (chloroform) 0.63.

(b) 12.23 g of 1-(trans-4-pentylcyclohexyl)-3-chloropropan-1-one and 112 mg of hydroquinone were dissolved in 120 ml of absolute dioxan in a sulphonation flask with stirrer, thermometer, reflux condenser, dropping funnel and nitrogen gasification [in an analogous manner to Chem. Ber. 109 (1976) 3426 and 111 (1978) 2825] and 12.6 g of triethylamine were added dropwise within 10 minutes. The mixture was subsequently stirred at 80° C. for 3.5 hours, cooled to 15° C., the precipitated triethylamine hydrochloride was filtered off under suction, back-washed with 50 ml of dioxan and the solvent was evaporated on a rotary evaporator. The oil obtained was taken up in 100 ml of chloroform, washed firstly with 100 ml of 5% sodium hydrogen carbonate solution and then with 100 ml of water (the aqueous phases were each extracted with a small amount of chloroform), dried over sodium sulphate and freed from solvent. The oily 1-(trans-4-pentylcyclohexyl)-2-propen-1-one obtained was further processed without additional purification.

(c) The foregoing crude 1-(trans-4-pentylcyclohexyl)-2-propen-1-one, 1.35 g of 3-benzyl-5-(2-hydroxyethyl)-4-methyl-1,3-thiazolium chloride [prepared according to H. Stetter et al., Synthesis 1975, 379] and 3.0 g of triethylamine were dissolved or suspended in 80 ml of absolute dioxane under nitrogen in a sulphonation flask with stirrer, thermometer, reflux condenser, dropping funnel and nitrogen gasification, heated to 80° C. and a solution of 7.5 g of caproic aldehyde in 20 ml of absolute dioxan was added dropwise at this temperature within 15 minutes. The mixture was subsequently boiled at reflux for 22 hours, then cooled to room temperature and the solvent was removed on a rotary evaporator. The residue was taken up in 150 ml of ether and washed successively with 100 ml of 1% sulphuric acid, 100 ml of 1% sodium hydroxide, 100 ml of 5% sodium hydrogen carbonate solution and 100 ml of water, the aqueous phases each being back-extracted with a small amount of ether. After drying the organic phases over sodium sulphate, the solvent was removed on a rotary evaporator. The brown oil obtained, which crystallized after cooling to 0° C., was recrystallized from 20 ml of ethanol at −20° C. There were obtained 8.8 g of light yellow crystals (m.p. 38°–40° C.). After evaporation of the solvent, the mother liquor was distilled in a high vacuum in a bulb-tube distillation apparatus, a further 4.1 g of yellow crystals being obtained in the main run (160°–170° C./0.04 mmHg). Total yield: 12.9 g of yellow 1-(trans-4-pentylcyclohexyl)nona-1,4-dione [83.8% based on 1-(trans-4-pentylcyclohexyl)-3-chloropropan-1-one]. By recrystallization from 20 ml of ethanol at −20° C. there were obtained 10 g of white crystals; m.p. 40°–41° C.; Rf value (chloroform) 0.64.

(d) 12.3 g of 1-(trans-4-pentylcyclohexyl)nona-1,4-dione were suspended in 90 ml of absolute ethanol in a sulphonation flask with stirrer, thermometer and reflux condenser and then a solution of 2.2 g of hydrazine hydrate in 10 ml of absolute ethanol was slowly added dropwise within 20 minutes. After completion of the addition, the mixture was stirred at 50° C. for a further 1 hour, cooled to room temperature and the solvent was removed on a rotary evaporator. The residue was dissolved in 250 ml of methylene chloride, washed with 100 ml of water and the aqueous phase was back-extracted twice with 50 ml of methylene chloride each time. The combined organic phases were dried over sodium sulphate and freed from solvent on a rotary evaporator. The resulting white-yellow residue (12.6 g) of 4,5-dihydro-3-pentyl-6-(trans-4-pentylcyclohexyl)-pyridazine was further processed without additional purification.

The following compounds can be manufactured in an analogous manner:

3-Propyl-6-(trans-4-pentylcyclohexyl)pyridazine; C-I 66.2° C.; virtual cl.p. about 14° C., 3-propyl-6-(trans-4-heptylcyclohexyl)pyridazine; C-I 54.5° C.; virtual cl.p. about 7° C., 3-heptyl-6-(trans-4-propylcyclohexyl)pyridazine; C-I 86.4° C.; virtual cl.p. about 0° C., 3-(p-pentylphenyl)-6-(trans-4-propylcyclohexyl)pyridazine; C-S 115° C.; S-I 201.5° C., 3-(trans-4-pentylcyclohexyl)-6-(trans-4-propylcyclohexyl)pyridazine; C-S 166.7° C.; S-I 196.5° C., 3-propyl-6-(trans-4-ethylcyclohexyl)pyridazine; m.p. 56.9° C., 3-propyl-6-(trans-4-butylcyclohexyl)pyridazine; m.p. 76.2° C., 3-(p-ethylphenyl)-6-(trans-4-pentylcyclohexyl)pyridazine; C-S 165.4° C., S-I 192° C., 3(p-pentylphenyl)-6-(trans-4-butylcyclohexyl)pyridazine; C-S 153.7° C., S-I 203° C. and 3-(p-propyloxyphenyl)-6-(trans-4-propylcyclohexyl)pyridazine C-S 151.7° C., S-I 219.6° C.

EXAMPLE 5

0.51 g of sodium was placed in a sulphonation flask with stirrer, thermometer, dropping funnel, reflux condenser and nitrogen gasification and 14 ml of n-pentanol were slowly added dropwise so that the alcohol boiled slightly (hydrogen evolution). Then, the mixture was heated to 60° C. in order to dissolve the sodium completely. After cooling to 30° C., a solution of 5.3 g of 3-chloro-6-(trans-4-pentylcyclohexyl)pyridazine in 50 ml of absolute benzene was added dropwise within 15 minutes and then the mixture was stirred at 60° C. for 4 hours. After cooling to room temperature, the mixture was concentrated on a rotary evaporator, the residue was taken up in 100 ml of methylene chloride and the solution obtained was washed twice with 100 ml of dilute sodium chloride solution each time (the aqueous phases were back-extracted with a small amount of methylene chloride). The organic phase was dried over sodium sulphate and evaporated on a rotary evaporator. The crude product obtained was chromatographed on silica gel with chloroform as the eluant and finally recrystallized several times from n-hexane/isopropanol (9:1) until absolutely pure. Yield: 4.8 g (75%) of white crystals of 3-pentyloxy-6-(trans-4-pentylcyclohexyl)-pyridazine (after a single recrystallization). M.p. 67.4° C.; virtual cl.p. about 6° C.; Rf value (chloroform/acetone 40:1) 0.6.

The 3-chloro-6-(trans-4-pentylcyclohexyl)pyridazine used as the starting material was prepared as follows:

(a) 48.9 g of 1-(trans-4-pentylcyclohexyl)-3-chloropropan-1-one (prepared according to Example 4) were dissolved in 350 ml of acetone in a round flask with reflux condenser and nitrogen gasification, 30.0 g of sodium iodide were added and the mixture was boiled at reflux for 1 hour. After cooling to room temperature, the mixture was concentrated on a rotary evaporator, the residue was taken up in 450 ml of absolute methanol and, after adding 14.3 g of potassium cyanide (spontaneous decolourization of the solution), the mixture was boiled at reflux for 2 hours. After cooling to room temperature, the solvent was evaporated, the residue was taken up in 350 ml of diethyl ether and washed twice with 150 ml of semi-concentrated sodium chloride solution each time. The aqueous phases were each back-extracted twice with 70 ml of diethyl ether. The combined organic phases were dried over sodium sulphate and evaporated to dryness. Recrystallization from 40 ml of ethyl acetate gave 27.25 g of white crystals. A further 8.75 g of white crystals were obtained by concentration of the mother liquor and recrystallization of the residue from 20 ml of hexane. Total yield: 36.0 g (76.6%) of γ-oxo-γ-(trans-4-pentylcyclohexyl)butyronitrile; m.p. 45°–46° C.; Rf value (chloroform) 0.45.

(b) 36.0 g of γ-oxo-γ-(trans-4-pentylcyclohexyl)-butyronitrile were dissolved in 400 ml of methanol in a sulphonation flask with stirrer, thermometer, dropping funnel and reflux condenser and a solution of 34.5 g of potassium hydroxide in 40 ml of water and 100 ml of methanol was added dropwise within 10 minutes. The mixture was subsequently boiled at reflux for 18 hours, cooled to room temperature and the solvent was removed on a rotary evaporator. The residue was taken up in 300 ml of water, acidified with 75 ml of concentrated hydrochloric acid and extracted firstly with 350 ml of methylene chloride and then with 150 ml of methylene chloride. The combined organic phases were washed twice with 200 ml of concentrated sodium chloride solution each time, dried over sodium sulphate and concentrated on a rotary evaporator. The light red coloured product was recrystallized from a solution of 120 ml of hexane and 110 ml of methylene chloride at −20° C., 27.8 g of white crystals being obtained. A further 2.4 g of crystals were obtained by concentration of the mother liquor and recrystallization of the residue from 50 ml of hexane and 30 ml of methylene chloride. Total yeild: 30.2 g (77.2%) of γ-oxo-γ-(trans-4-pentylcyclohexyl)butyric acid; m.p. 113°–114° C.; Rf value (chloroform/acetone 2:1) 0.58.

(c) 56.6 g of γ-oxo-γ-(trans-4-pentylcyclohexyl)-butyric acid were dissolved in 500 ml of absolute ethanol in a sulphonation flask with stirrer, thermometer and reflux condenser, treated with 25 ml of hydrazine hydrate and boiled at reflux for 1.25 hours. After cooling to room temperature, the mixture was diluted with 750 ml of water, the separated precipitate was filtered off under suction, washed with a large amount of water and the still moist residue was crystallized from 80 ml of absolute ethanol at −20° C. Yield: 48.7 g (87.4%) of white crystals of 6-(trans-4-pentylcyclohexyl)-4,5-dihydro-3(2H)-pyridazinone; m.p. 152°–153° C.; Rf value (chloroform/acetone 2:1) 0.46.

(d) 47.5 g of 6-(trans-4-pentylcyclohexyl)-4,5-dihydro-3-(2H)-pyridazinone were dissolved in 140 ml of glacial acetic acid in a sulphonation flask with stirrer, thermometer, reflux condenser and dropping funnel and heated to 60° C. 33.4 g of bromine were subsequently added dropwise within 45 minutes, whereby a slight exothermic reaction set in immediately and further heating could accordingly be dispensed with. A white precipitate formed after a short time. After completion of the bromine addition, the mixture was stirred at 60° C. for a further 2 hours, then cooled to room temperature, the yellow coloured precipitate was filtered off under suction and washed with 200 ml of cold ethyl acetate. The almost white suction filter material was stirred well in 150 ml of dilute ammonia, suction filtered and washed with a large amount of water. The well pressed-out, still moist suction filter material was dissolved in 100 ml of hot absolute ethanol and filtered and then brought to crystallization by slowly cooling to −20° C., 41.8 g of white crystals being obtained. Concentration of the mother liquor and recrystallization of the residue from 10 ml of absolute ethanol gave a further 2.1 g of crystals. Total yield: 43.9 g (93%) of 6-(trans-4-pentylcyclohexyl)-3(2H)-pyridazinone; m.p. 124°-127° C.; Rf value (chloroform/acetone 2:1) 0.34.

(e) 19.85 g of 6-(trans-4-pentylcyclohexyl)-3(2H)-pyridazinone were suspended in 80 ml of absolute benzene at 30° C. in a sulphonation flask with stirrer, thermometer, reflux condenser and dropping funnel and 24.6 g of phosphorus oxychloride were added dropwise while stirring well within 30 minutes, whereby immediately an exothermic reaction and hydrogen chloride evolution set in and the temperature rose to 45° C. The temperature was subsequently increased slowly to 80° C. and the mixture was stirred at this temperature for 4 hours. After cooling to room temperature, the clear dark brown mixture was poured on to 200 g of ice, the benzene phase was separated and the aqueous phase was extracted twice with 100 ml of diethyl ether each time. The combined organic phases were washed with 100 ml of saturated sodium hydrogen carbonate solution and 100 ml of water (the aqueous phases were back-extracted with a small amount of diethyl ether), dried over sodium sulphate and evaporated. The brown coloured residue was recrystallized from 15 ml of methylene chloride and 15 ml of hexane at −20° C. There were obtained 9.1 g of white crystals which were washed well with hexane cooled to −20° C. Concentration of the mother liquor and recrystallization of the residue from 20 ml of hexane gave a further 7.25 g of white crystals. Total yield: 16.35 g (76.7%) of 3-chloro-6-(trans-4-pentylcyclohexyl)pyridazine; m.p. 81°-89° C.; Rf value (chloroform/acetone 2:1) 0.7.

The following compound can be manufactured in an analogous manner:
3-Ethoxy-6-(trans-4-pentylcyclohexyl)pyridazine; m.p. 59.5° C.; virtual cl.p. about 0° C.

EXAMPLE 6

6.16 g of 1-(trans-4-heptylcyclohexyl)hepta-1,4-dione (prepared analogously to Example 4) were dissolved in 50 ml of absolute ethanol in a sulphonation flask with stirrer, thermometer, dropping funnel, reflux condenser and nitrogen gasification and then a solution of 1.1 g of hydrazine hydrate in 10 ml of absolute ethanol was added dropwise at 0° C. within 10 minutes, a white precipitate of the dihydropyridazine forming. The mixture was stirred at 50°-60° C. for a further 1 hour in order to complete the reaction.

After cooling to 40° C., the mixture was treated with 0.5 g of palladium/carbon and heated to 60° C. for about 2 hours (hydrogen evolution). After completion of the reaction, the mixture was cooled to room temperature, the palladium/carbon was filtered off under suction and back-washed with ethanol and the filtrate was evaporated to dryness on a rotary evaporator. The residue was taken up in 150 ml of methylene chloride, washed successively with 100 ml of 0.2 N hydrochloric acid, 100 ml of 5% sodium hydrogen carbonate solution and 100 ml of water (the aqueous phases were each back-extracted with a small amount of methylene chloride) and dried over sodium sulphate. After evaporation of the solvent, the crude product (6.1 g) was chromatographed on silica gel with chloroform as the eluant. There were thereby obtained 4.7 g (77.6%) of 3-propyl-6-(trans-4-heptylcyclohexyl)pyridazine which was stirred in 50 ml of methylene chloride with 1 g of active carbon, suction filtered, evaporated and recrystallized several times more from a small amount of n-pentane at −20° C. Yield of pure substance 3.1 g (51%); C-I 54.5° C.; virtual cl.p. about 7° C.

All pyridazines set forth in Example 4 can be manufactured in an analogous manner.

We claim:
1. A compound of the formula

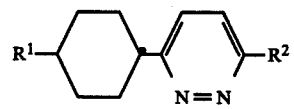

wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and said alkyl and alkoxy groups in $R^2$ each are straight-chain groups of 1 to 10 carbon atoms.

2. The compound of claim 1 wherein $R^2$ is alkyl, alkoxy or p-alkylphenyl.

3. The compound of claim 1 wherein the alkyl and alkoxy in the $R^2$ moieties each are straight-chain of 1 to 7 carbon atoms.

4. The compound of claim 1 wherein $R^1$ is straight-chain alkyl of 3 to 9 carbon atoms.

5. The compound of claim 4 wherein $R^1$ is straight-chain alkyl of 3 to 7 carbon atoms.

6. The compound of claim 1 wherein $R^1$ is straight-chain alkyl of 3 to 7 carbon atoms and $R^2$ is straight-chain alkyl of 1 to 7 carbon atoms.

7. The compound of claim 1 wherein $R^2$ is p-alkylphenyl and the alkyl group therein is straight-chain alkyl of 1 to 7 carbon atoms.

8. The compound of claim 1, 3-propyl-6-(trans-4-ethylcyclohexyl)pyridazine.

9. The compound of claim 1, 3-propyl-6-(trans-4-pentylcyclohexyl)pyridazine.

10. The compound of claim 1, 3-propyl-6-(trans-4-heptylcyclohexyl)pyridazine.

11. The compound of claim 1, 3-pentyl-6-(trans-4-pentylcyclohexyl)pyridazine.

12. A liquid crystal mixture comprising a compound of the formula

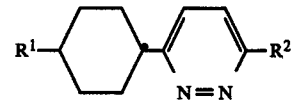

wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and said alkyl and alkoxy groups in $R^2$ each are straight-chain groups or 1 to 10 carbon atoms.

13. The liquid crystal mixture of claim 12, wherein the dielectric anisotropy of the total mixture is negative.

14. The liquid crystal mixture of claim 12 comprising (a) a compound of the formula

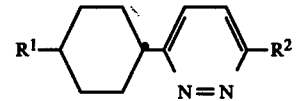

wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and said alkyl and alkoxy groups in $R^2$ each are straight-chain groups of 1 to 10 carbon atoms; and (b) a nematic compound or mixture having a dielectric anisotropy of at most about +1.

15. The liquid crystal mixture of claim 14 comprising
(a) a compound of the formula

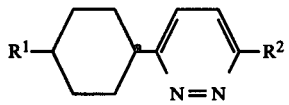   I wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and said alkyl and alkoxy groups in $R^2$ each are straight-chain groups of 1 to 10 carbon atoms (b) a nematic compound or mixture having a dielectric anistropy of about −3 to +1; and (c) a compound or mixture having a cross-over frequency of about 100 Hz to about 20 kHz and having a positive dielectric anisotropy of more than about 10 at frequencies below the cross-over frequency of the total mixture.

16. The liquid crystal mixture of claim 14 wherein said nematic compound or mixture having a dielectric anisotropy of at most about +1 is one or more compounds selected from the group consisting of

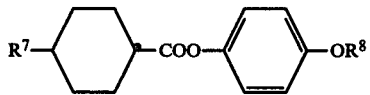   XXV

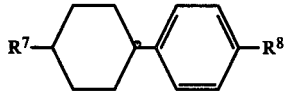   XXVI

   XXVII

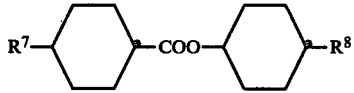   XXVIII

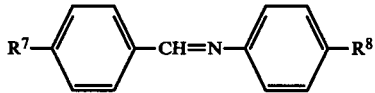   XXIX

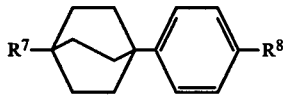   XXX wherein, in each of formulas XXV through XXX $R^7$ and $R^8$ each are straight-chain alkyl of 1 to 8 carbon atoms

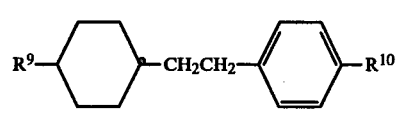   XXXI wherein $R^{10}$ is $-R^{11}$ or $-OR^{11}$ and $R^9$ and $R^{11}$ each are straight-chain alkyl of 1 to 12 carbon atoms

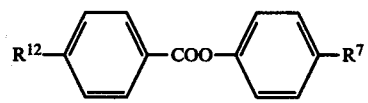   XXXII wherein $R^{12}$ is straight-chain alkyl of 1 to 8 carbon atoms or straight-chain alkanoyloxy of 2 to 9 carbon atoms and $R^7$ is straight-chain alkyl of 1 to 8 carbon atoms

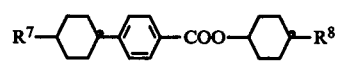   XXXIII

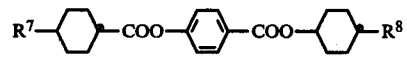   XXXIV and

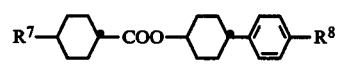   XXXV wherein, in each of formulas XXXIII through XXXV $R^7$ and $R^8$ each are straight-chain alkyl of 1 to 8 carbon atoms.

17. The liquid crystal mixture of claim 15 wherein said compound or mixture having a cross-over frequency of about 100 Hz to about 20 kHz and a dielectric anisotropy of more than about 10 is:

a compound of the formula

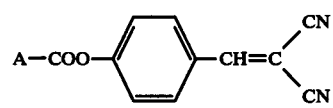   XXII wherein A represents a group of the formula

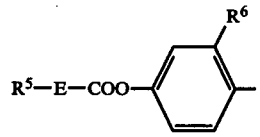   XXIII or

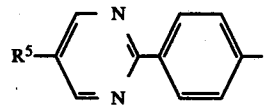   XXIV wherein $R^5$ alone is straight-chain alkyl of 1 to 12 carbon atoms and $R^6$ is fluorine, chlorine, bromine or cyano and $R^5$—E is p-alkylphenyl, trans-4-alkylcyclohexyl, 4'-alkyl-4-biphenylyl, p-(trans-4-alkylcyclohexyl)phenyl or p-(5-alkyl-2-pyrimidinyl)phenyl.

18. An electro-optical cell having two plate means at least one plate means being transparent; means for controlling the optical activity of the cell; and liquid crystal means including a compound of the formula

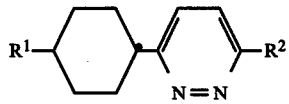

wherein $R^1$ is straight-chain alkyl of 1 to 12 carbon atoms, $R^2$ is alkyl, alkoxy, p-alkylphenyl, p-alkoxyphenyl or trans-4-alkylcyclohexyl, and said alkyl and alkoxy groups in $R^2$ each are straight-chain groups of 1 to 10 carbon atoms.